(12) United States Patent
Kamiyama

(10) Patent No.: US 6,290,648 B1
(45) Date of Patent: Sep. 18, 2001

(54) ULTRASONIC DIAGNOSTIC APPARATUS

(75) Inventor: Naohisa Kamiyama, Otawara (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/411,848

(22) Filed: Oct. 4, 1999

(30) Foreign Application Priority Data

Oct. 5, 1998 (JP) .................................................. 10-282614

(51) Int. Cl.$^7$ ...................................................... A61B 8/00

(52) U.S. Cl. ........................................... 600/443; 128/916

(58) Field of Search ............................ 128/916; 600/443, 600/444, 441, 447, 449

(56) References Cited

U.S. PATENT DOCUMENTS

| | | | |
|---|---|---|---|
| 5,706,816 | * 1/1998 | Mochizuki et al. | .................. 600/443 |
| 5,860,924 | * 1/1999 | Quistgaard | ............................ 600/441 |
| 5,876,342 | * 3/1999 | Chen et al. | ........................... 600/443 |
| 6,123,669 | * 9/2000 | Kanda | ................... 600/443 |

OTHER PUBLICATIONS

R. W. Prager, et al., "Rapid Calibration for 3–D Freehand Ultrasound", Ultrasound in Med. & Biol., vol. 24, No. 6, 1998, pp. 855–869.

* cited by examiner

*Primary Examiner*—Marvin M. Lateef
*Assistant Examiner*—Maulin Patel
(74) *Attorney, Agent, or Firm*—Oblon, Spivak, McClelland, Maier & Neustadt, P.C.

(57) ABSTRACT

An ultrasonic diagnostic apparatus acquires an echo signal by scanning a scanning plane inside an object to be examined with an ultrasonic beam via an ultrasonic probe, generates two-dimensional ultrasonic image data on the basis of this echo signal, and displays this two-dimensional ultrasonic image data as a two-dimensional ultrasonic image. A point of interest is sometimes set on this image, and the scanning plane is sometimes changed by moving the ultrasonic probe. In this invention, whether the point of interest is contained in the changed scanning plane is checked on the basis of the three-dimensional position of the changed scanning plane and the three-dimensional position of the point of interest. If the point of interest is contained in the changed scanning plane, a mark representing the point of interest is displayed by synthesis by matching the position with tomographic image data corresponding to this changed scanning plane. This allows an operator to understand a change in the positional relationship between the scanning planes before and after the change of the scanning planes.

18 Claims, 8 Drawing Sheets

ULTRASONIC DIAGNOSTIC APPARATUS

BACKGROUND OF THE INVENTION

The present invention relates to an ultrasonic diagnostic apparatus for scanning the three-dimensional region of an object to be examined with ultrasonic pulses to perform various diagnoses using the resultant information.

Various apparatuses are available as medical applications of ultrasonic waves. The most frequently used is an ultrasonic diagnostic apparatus which obtains tomographic images of soft tissues of living bodies by using the ultrasonic pulse reflection method. This ultrasonic diagnostic apparatus displays a tomographic image of a tissue by a noninvasive examination method. Compared with other diagnostic apparatuses such as an X-ray diagnostic apparatus, an X-ray computer tomographic apparatus (X-ray CT), a magnetic resonance imaging apparatus (MRI), and a nuclear medicine diagnostic apparatus (e.g., a gamma camera and SPECT), an ultrasonic diagnostic apparatus has the advantages that it can display images in real time, is small and inexpensive, has high safety with no exposure to x-rays, and is capable of blood flow imaging by using the ultrasonic Doppler method.

For these reasons, ultrasonic diagnoses are extensively performed in examinations of hearts, abdomens, mammary glands, and urinary organs, and in obstetrics and gynecology. In particular, heart beats and the motions of an unborn child can be displayed in real time with a simple operation of bringing an ultrasonic probe into contact with the body surface, and the safety is high. Therefore, examinations can be repetitively performed and can also be readily performed even on the bedside.

It is also possible to display the velocity distribution of a blood flow which moves closer to or away from a vibrator by using the ultrasonic Doppler method and display the power value distribution of a blood flow echo signal by using the power Doppler method. In particular, the power Doppler method can detect the perfusion of a blood vessel system with high sensitivity and hence is used to diagnose peripheral blood flow abnormality of a kidney and hepatoma.

In the field of these ultrasonic diagnoses, as in X-ray CT and MRI, needs for three-dimensional images are increasing. Three-dimensional images have information in the direction of depth in addition to planar information obtained from two-dimensional tomographic images. Accordingly, three-dimensional images are expected to allow an operator to more clearly observe the shape of a tissue, circulation of the blood, and the like.

Three-dimensional information is acquired as follows. That is, a position sensor attached to a probe is used to obtain position information and corresponding image information at the same time. After that, a three-dimensional image is reconstructed on the basis of the position information. Many methods have been proposed so far, and it has become possible to reconstruct and display three-dimensional images within very short time periods with the aid of increased operating speeds of recent CPUs.

Although the operating speeds of CPUs have increased, however, it is currently still impossible to reconstruct and display a three-dimensional image in real time, or in almost real time, from three-dimensional echo data input by three-dimensional scan. In practice, therefore, it is necessary to employ a method which reconstructs and displays a three-dimensional image after three-dimensional data is input and scan is stopped. Accordingly, in ordinary diagnoses, conventional two-dimensional tomographic images are observed in real time in most cases.

BRIEF SUMMARY OF THE INVENTION

It is an object of the present invention to effectively use three-dimensional position information of a scanning plane in various forms while displaying tomographic images by attaching importance to the advantage of real-time observation.

In the present invention, a mark representing a point of interest or a region of interest is designated on an image of a certain scanning plane. When this scanning plane is changed to another, the mark is displayed on an image of the changed scanning plane if the point of interest is contained in this changed scanning plane. If the point of interest is not contained in the changed scanning plane, no mark is displayed on the image of this changed scanning plane. Therefore, an operator can recognize the three-dimensional positional relationship between images of different scanning planes to a certain degree.

In the present invention, an image in the same slice of an image that is being displayed in real time is generated from volume data previously acquired before scanning, and this image is displayed simultaneously with the image that is being displayed in real time. Hence, when past data of the same patient is held as the volume data, the transition of a lesion can be easily recognized. Also, a lesion can be readily found when data of a healthy person is held as the volume data. Furthermore, when data collected from the same patient immediately before diagnosis is held as the volume data, scan of the same slice can be readily reproduced. That is, various effects can be achieved in accordance with applications.

In the present invention, a partial image in the same position as an image that is being displayed in real time is cut out from volume data previously acquired before scanning. This partial image is displayed as it is synthesized on the image that is being displayed in real time. Accordingly, when data of a different patient who has become ill is held as the volume data, this data can be used in educational simulation of ultrasonic diagnoses for healthy persons.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Embodiments of the present invention will be described below with reference to the accompanying drawings. Although the present invention is applicable to all portions of interest, in the following description it is assumed that an abnormal portion is identified by observing a tumor in a liver or in a spleen or by observing a blood vessel.

First Embodiment

Figure 1:
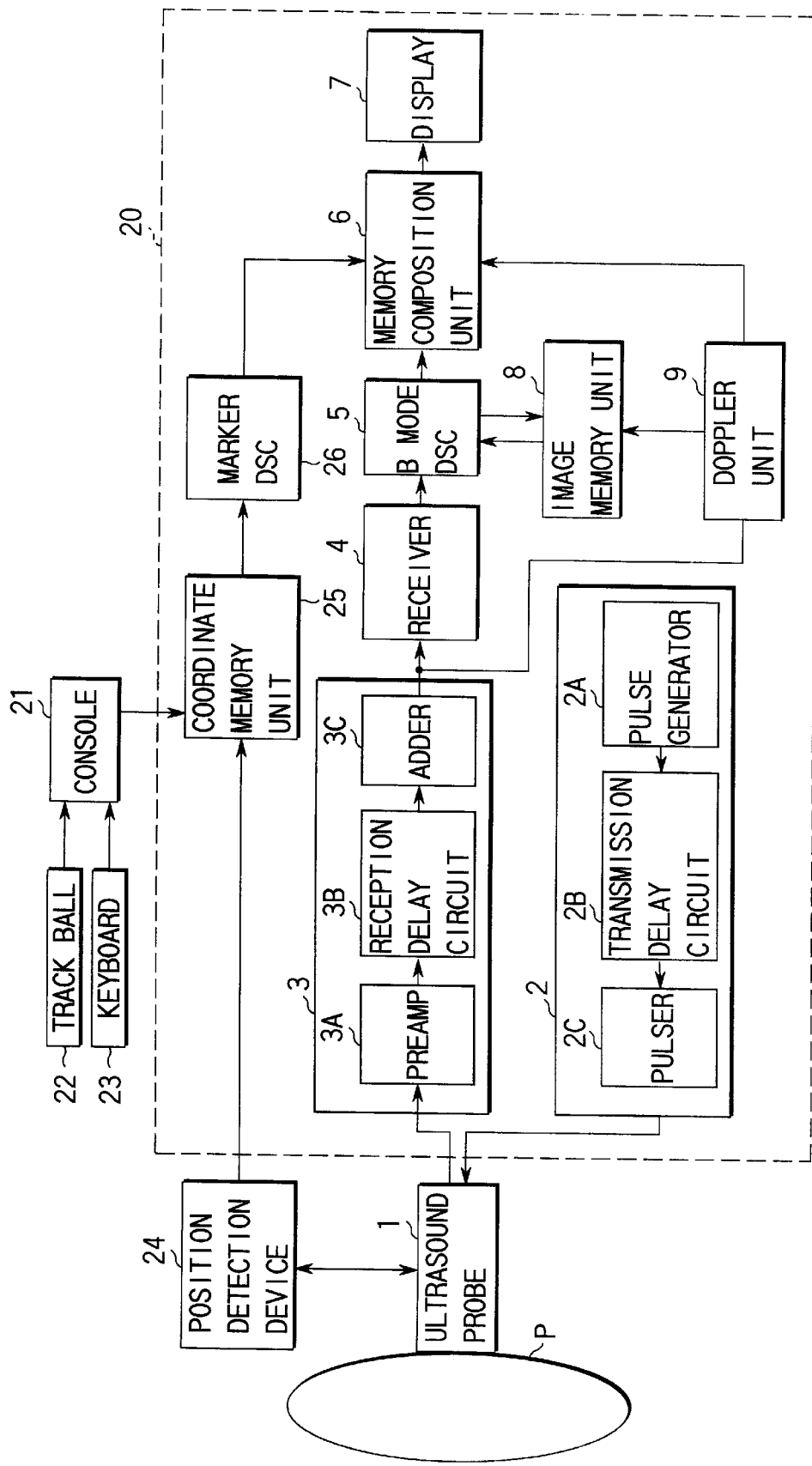
FIG. 1 is a block diagram showing the arrangement of an ultrasonic diagnostic apparatus according to the first embodiment of the present invention.

FIG. 1 shows the arrangement of an ultrasonic diagnostic apparatus according to the first embodiment. This apparatus is composed of an ultrasonic probe 1, an apparatus main body 20, and a console 21. The ultrasonic probe 1 transmits ultrasonic signals to an object to be examined and receives echo signals from the object. The apparatus main body 20 drives the ultrasonic probe 1 and processes echo signals collected via this ultrasonic probe 1. The console 21 is connected to the apparatus main body 20 to input various pieces of instructive information from an operator to the apparatus main body 20. various input devices such as a trackball 22 and a keyboard 23 are connected to or installed in the console 21. Scanning conditions, regions of interest, and other various settingconditions concerning the present invention are input via this console 21.

A plurality of fine vibrators such as piezoelectric ceramic elements are arrayed in the end portion of the ultrasonic probe 1. The form of this ultrasonic probe 1 can be any of sector compatible, linear compatible, and convex compatible. In this embodiment, assume that the ultrasonic probe 1 is sector compatible.

The apparatus main body 20 includes an ultrasonic transmitting unit 2, an ultrasonic receiving unit 3, a receiver 4, a B mode digital scan converter 5, a memory composition unit 6, a display 7, an image memory unit 8, and a Doppler unit 9. In addition to these general components, this apparatus main body 20 further includes a position detection device 24, a coordinate memory unit 25, and a marker digital scan converter 26, each of which is related to the present invention.

The ultrasonic transmitting unit 2 has a pulse generator 2A, a transmission delay circuit 2B, and a pulser 2C. The ultrasonic transmitting unit 2 controls the delay time of each channel to shape an ultrasonic wave into the form of a beam, and transmits this beam as a pulse wave to an object to be examined. The ultrasonic transmitting unit 2 also changes the direction of this ultrasonic beam to scan slices in an object to be examined. An ultrasonic beam transmitted from the ultrasonic probe 1 by driving this ultrasonic transmitting unit 2 is reflected by a discontinuous plane of acoustic impedance in an object to be examined, and returned to the ultrasonic probe 1.

Small electrical signals (echo signals) converted by the individual vibrators of the ultrasonic probe 1 are supplied to the ultrasonic receiving unit 3 in units of channels. In this ultrasonic receiving unit 3, these signals are amplified by a preamplifier 3A, given the same delay time as in the transmission by a reception delay circuit 3B, and finally added by an adder 3C. This addition generates a reception signal in which a reflected component in a specific direction is emphasized.

The receiver 4 receives this reception signal, logarithmically amplifies the signal, and detects the envelope. An analog-to-digital converter outputs the resultant signal as a digital signal. The B mode digital scan converter (DSC) 5 converts the output from the receiver 4 from an ultrasonic-scan raster signal string to a video-format raster signal string. In this manner, tomographic image data, i.e., so-called B mode image data is generated. This tomographic image data is supplied to the display 7 via the memory composition unit 6 and displayed in black and white. Note that a so-called color Doppler image representing circulation of the blood (blood flow distribution) can be used instead of B mode image data.

The reception signal generated by the ultrasonic receiving unit 3 is also supplied to the Doppler unit 9 where the signal is first subjected to orthogonal phase detection and then converted into a digital signal. An MTI filter removes a low-frequency component (clutter component) subjected to frequency shift due to reflection by a slow moving body, such as a heart wall, other than a Doppler examination object; the MTI filter passes only a high-frequency component (blood flow component) subjected to frequency deviation due to reflection by a fast moving body, such as a blood cell, as a Doppler examination object. Furthermore, an autocorrelator analyzes the frequencies of this blood flow component and obtains the intensity of each frequency. On the basis of this intensity of each frequency, the average velocity, dispersion, and power are calculated. In this way, blood flow image data representing the state of a two-dimensional blood flow is generated. The memory composition unit 6 synthesizes this blood flow image data on the tomographic image data. The display 7 displays the synthetic data in colors.

The image memory unit 8 stores one or both of the ultrasonic-scan raster signal string data before conversion by the B mode digital scan converter 5 and the video-format raster signal string data after conversion. An operator can freely read out and display these data after diagnosis or the like.

Next, the position detection unit 24, the coordinate memory unit 25, and the marker digital scan converter 26 as the main parts of this embodiment will be described below together with the mechanism of three-dimensional scan.

(Three-Dimensional Scan)

Figure 2:
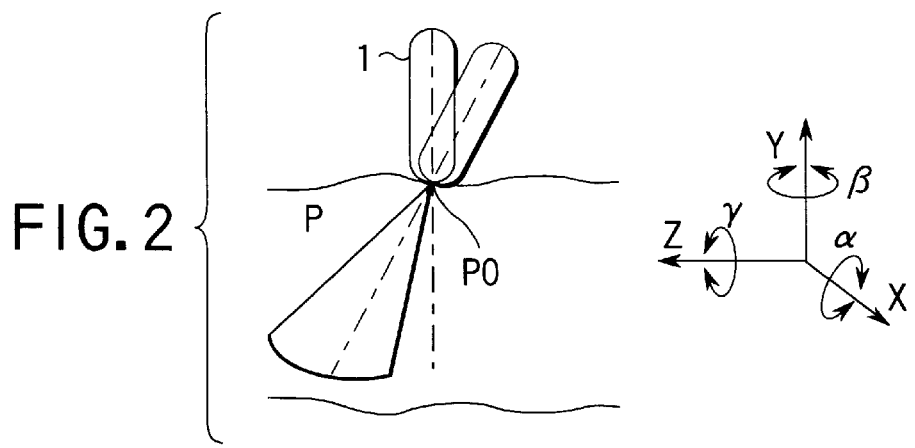
FIG. 2 is a schematic view showing general three-dimensional scan performed by moving a probe 1 shown in FIG. 1.

FIG. 2 is a view showing an example of this three-dimensional scan. In three-dimensional scan, a scanning plane is moved in a three-dimensional region of an object P to be examined, and reception signals from different points in this three-dimensional region are collected. In this embodiment, three-dimensional scan is performed by bringing the tip of the probe 1 into contact with the body surface of the object and, while this position (to be referred to as a reference position P0 hereinafter) is fixed, moving the probe 1 by appropriately combining rotation $\alpha$ about an X-axis (horizontally perpendicular to the body axis of the object P) of the probe 1, rotation $\mu$ about a Y-axis (vertically perpendicular to the body axis of the object P) of the probe 1, and rotation $\gamma$ about a Z-axis (parallel to the body axis of the object P) of the probe 1.

(Slice Position Detection)

During three-dimensional scan, the position detection device 24 constantly or periodically detects the reference position P0 (x0, y0, z0) of the probe 1, an angle $\theta\alpha$ (a rotational angle about the X-axis), an angle $\theta\beta$ (a rotational angle about the Y-axis), and an angle $\theta\gamma$ (a rotational angle about the Z-axis). These detection signals (to be referred to as position information hereinafter) represent the position of a slice to be scanned with an ultrasonic beam.

(Acquisition and Storage of Three-Dimensional Position Information of Point of Interest or Region of Interest).

Figure 3A:
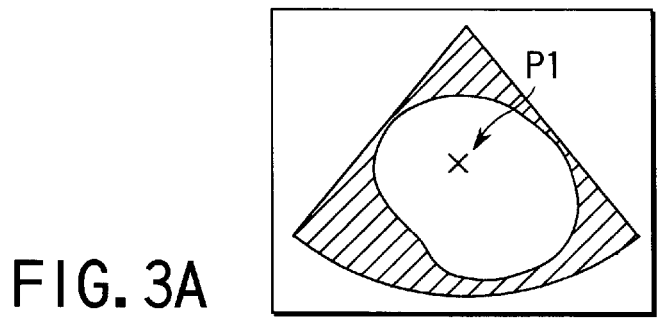
FIG. 3A is a view showing a point mark P1 designated in a given position on a real-time image via, e.g., a trackball 22 shown in FIG. 1.

As shown in FIG. 3A, the coordinate memory unit 25 outputs mark data when an operator operates the console 2 or the like to designate, by using a pointer (cursor), a point of interest such as a tumor on a tomographic image displayed on the display 7. The memory composition unit 6 synthesizes this mark data on the tomographic image data via the marker digital scan converter 26. Consequently, a mark P1 is superposed on the point of interest on the tomographic image. Note that the shape of this mark is not limited to X but can by any arbitrary shape such as a circle, a polygon, or an arrow. Note also that the point of interest need not be one, i.e., a plurality of points (P2, P3, . . . ) can be designated. Furthermore, points of interest can be continuously set on the contour of a region such as an organ or a tumor. Moreover, a region of interest can be set instead of a point of interest. This region of interest can be specified by a trace line representing the contour of a region such as an organ or tumor.

Figure 3B:
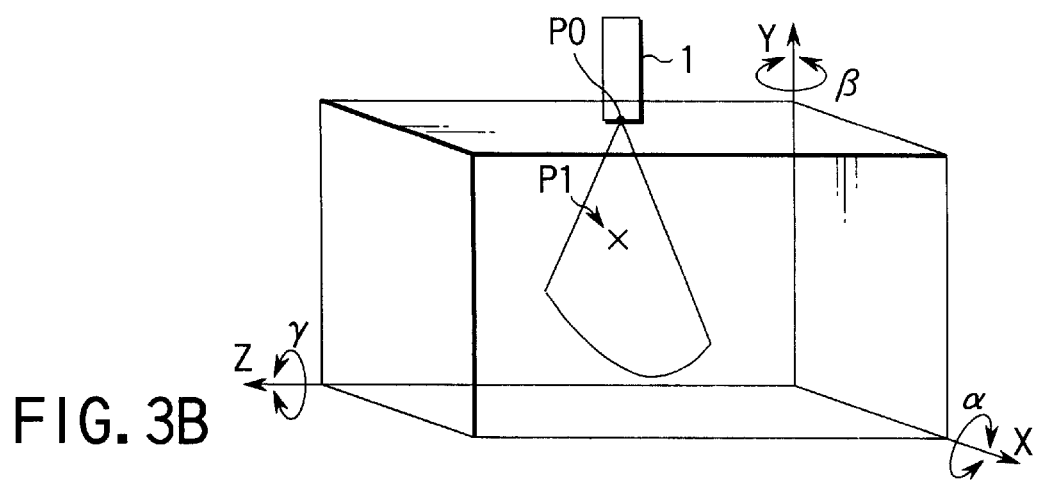
FIG. 3B is a view showing the position of the point mark P1 detected by a position detection device 24 shown in FIG. 1.

The coordinate memory unit 25 obtains the position of the mark in a frame. On the basis of this position and the slice position detected by the position detection device 24, the coordinate memory unit 25 calculates and stores the three-dimensional coordinates (position information) of the point of interest shown in FIG. 3B.

(Mark Redisplay)

After a point of interest is designated on a tomographic image of a certain slice and position information of this point of interest is stored, the scanning plane is sometimes changed to, e.g., observe a tumor or the like in a different direction. The position detection device 24 detects position information of this changed scanning plane and supplies the detection information to the coordinate memory unit 25. On the basis of the stored position information of the point of interest and the position information of the changed scanning plane, the coordinate memory unit 25 checks whether the point of interest is contained in the changed scanning plane. If the point of interest is not contained in the changed scanning plane, the coordinate memory unit 25 does not output mark data. Consequently, no mark is displayed in a tomographic image of the changed scanning plane. On the other hand, if the point of interest is contained in the changed scanning plane, the coordinate memory unit 25 outputs mark data. Consequently, a mark is displayed as it is superposed on the tomographic image of the changed scanning plane.

Accordingly, the three-dimensional positional relationship between tomographic images of different scanning planes can be recognized to some extent via marks. This achieves the following effects:

A tumor can be easily found when it is to be again observed in a different slice.

When a constricted portion of a blood vessel is to be again observed in a different slice, the positional relationship between blood vessels is readily observable.

Lesions in an organ can be accurately counted with no overlapping counting.

An operator can use the apparatus relatively easily in conventional diagnoses because diagnoses are performed using conventional 2D tomographic images with no three-dimensional images appearing.

(Another Example of Mark)

Figure 4A:
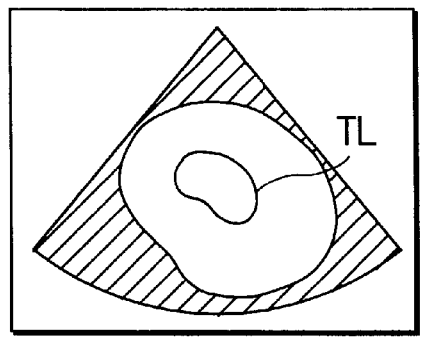
FIG. 4A is a view showing a trace line mark TL freely drawn on a real-time image via, e.g., the trackball 22 shown in FIG. 1.
Figure 4B:
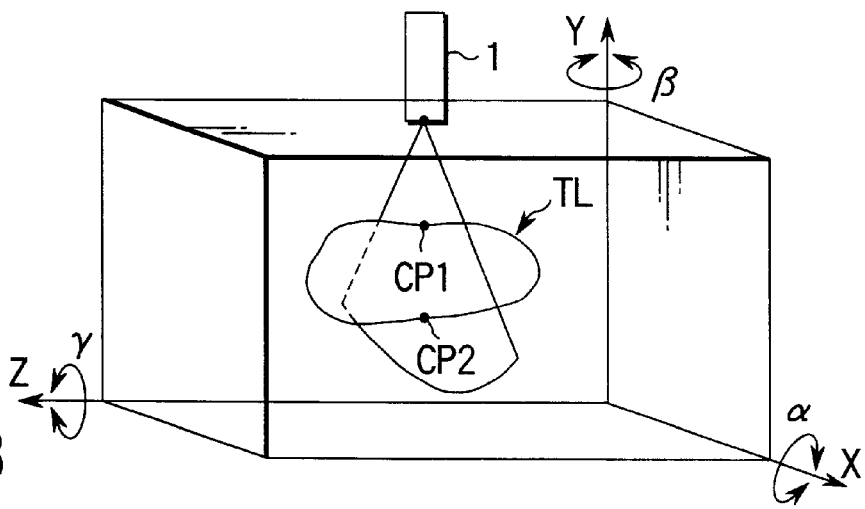
FIG. 4B is a view showing the trace line TL of FIG. 4A and cross points CP1 and CP2 to a scanning plane different from that when the trace line TL is drawn.
Figure 4C:
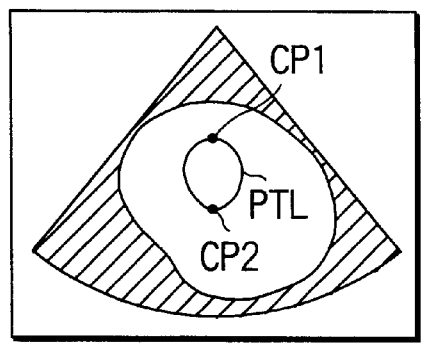
FIG. 4C is a view showing cross point marks CP1 and CP2 displayed on an image corresponding to the scanning plane shown in FIG. 4B and a trace line mark PTL projected on this scanning plane.

As shown in FIG. 4A, a mark can also be a trace line (TL) of a region of interest such as a blood vessel slice or a tumor contour. This mark is superposed on a tomographic image as follows. For example, regarding the trace line TL as N points (P11, P12, . . . , P1N), whether the changed scanning plane intersects the trace line TL is checked (FIG. 4B) as in the case of P1 described above. If the changed scanning line intersects the trace line TL, marks CP1 and CP2 representing the intersections are superposed on a tomographic image (FIG. 4C).

Alternatively, the trace line TL is projected on the changed scanning plane, and this projected trace line PTL is superposed on the tomographic image.

(Enlargement of Region of Point of Interest)

In strictly determining whether a point of interest is contained in the changed scanning plane as described above, no mark is displayed even if the point of interest slightly deviates from the changed scanning plane. This makes a point of interest difficult to handle. Therefore, instead of being handled as a point represented by (P1)=(x1, y1, z1)

a point of interest is enlarged to a region represented by

Area (P1)=(x1±σ, y1±σ, z1±σ)

In this case, it is possible to moderately check whether this enlarged region intersects the changed scanning plane. Note that an arbitrary enlargement parameter σ can be designated by an operator.

(Proximity Display)

As an example of expansion of the aforementioned enlargement of a point of interest, it is possible to display that a scanning plane is close to a point of interest. For example, with respect to the point of interest P1 designated by an operator, two types of areas centered on this position are set as Area1 (P1)=(x1±σ1, y1±σ1, z1±σ1)

and

Area2 (P1)=(x1±σ2, y1±σ2, z1±σ2)

where σ<σ1<σ2.

The display mode, shape, or color of a mark is changed in accordance with whether the area Area2 (P1) intersects the changed scanning plane, the area Area1 (P1) intersects the changed scanning plane, or the point of interest P1 is contained in the changed scanning plane. This allows the operator to recognize that the scanning plane is close to the mark or gradually moves closer to or away from the mark. More specifically, if the scanning plane intersects the area Area2 (P1), a relatively small mark is displayed; if the scanning plane intersects the area Area1 (P1), a relatively large mark is displayed. This comparatively facilitates finding a previously designated point of interest from a different scanning plane. Note that this method is also realizable for the color Doppler method.

(Modification of Position Detection Device 24)

Figure 5:
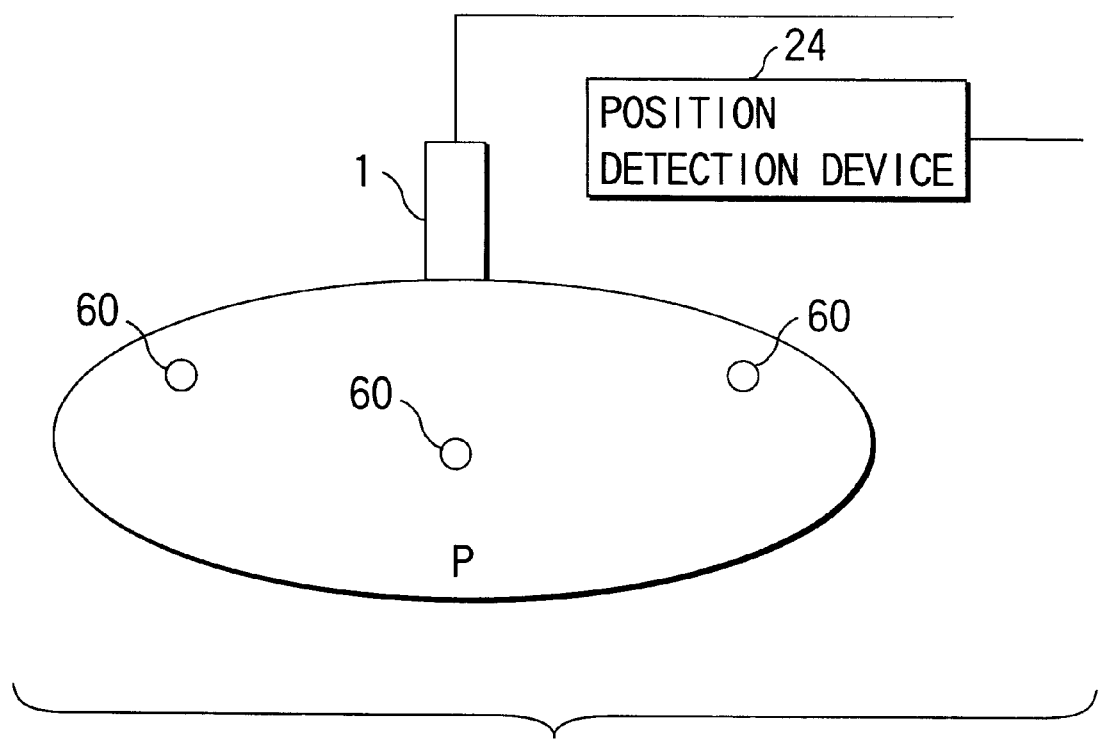
FIG. 5 is a view showing another arrangement of the position detection device 24 shown in FIG. 1.

The position detection device 24 detects a relative position with respect to the probe 1. If, therefore, the absolute position of the object P moves, it is possible that position matching error occurs and a mark deviates from a real-time image. Accordingly, as shown in FIG. 5, position sensors 60 are attached to at least three portions of the object P. This allows the position detection device 24 to simultaneously detect the positions of both the object P and the probe 1 and always correct the object-probe positional relationship.

Second Embodiment

Figure 6:
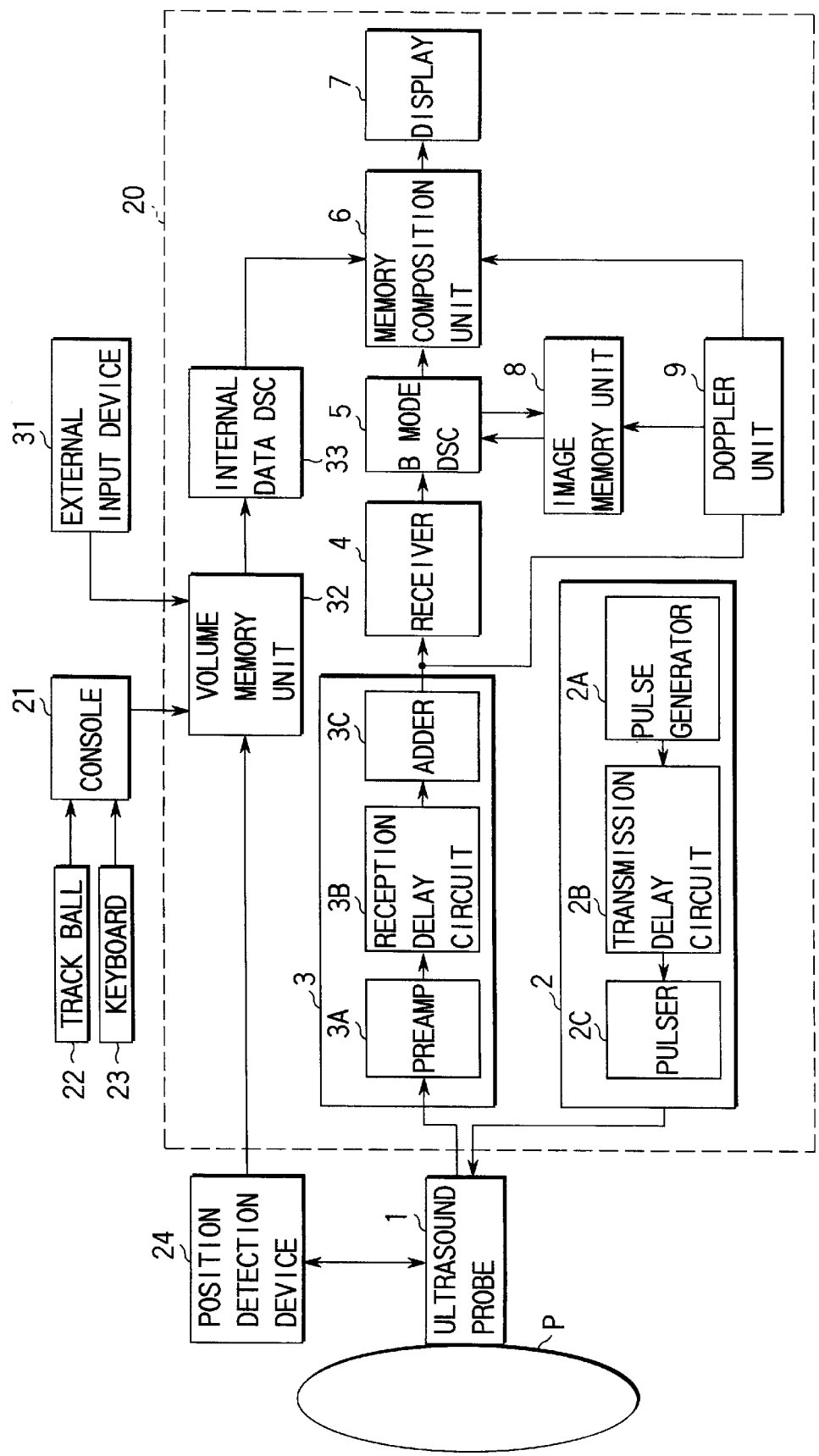
FIG. 6 is a block diagram showing the arrangement of an ultrasonic diagnostic apparatus according to the second embodiment of the present invention.

FIG. 6 shows the arrangement of an ultrasonic diagnostic apparatus according to the second embodiment. In FIG. 6, the same reference numerals as in FIG. 1 denote the same parts, and a detailed description thereof will be omitted. An apparatus of this second embodiment includes an external input device 31, a volume memory unit 32, and an internal data digital scan converter 33. The volume memory unit 32 stores past ultrasonic volume data of, e.g., the heart and the abdominal part of the same patient, which is input from an electronic crate or an image database via the external input device 31 having a network protocol function. Alternatively, the volume memory unit 32 stores volume data generated from ultrasonic image data of the same patient, which is collected immediately before diagnosis. This volume data need not be data obtained by the ultrasonic diagnostic apparatus but can be data obtained by another modality such as an X-ray computer tomographic imaging apparatus (CT scan) or a magnetic resonance imaging apparatus (MRI).

In accordance with scanning plane position information detected by a position detection device 24, the volume memory unit 32 selectively reads out data in the slice from the volume data. From this readout data, the internal data digital scan converter 33 reconstructs tomographic image data in the same slice as the scanning plane detected by the position detection device 24, i.e., the slice that is being scanned in real time.

Since the position detection device 24 detects position information in real time, a tomographic image to be reconstructed on the basis of the volume data also changes in accordance with the movement of the scanning plane corresponding to the motion of a probe 1.

A memory composition unit 6 matches the image quality (e.g., resolution and luminance level) of the tomographic image data reconstructed by the internal data digital scan converter 33 with that of the real-time tomographic image data, and synthesizes the two image data parallel in one frame. A display 7 displays this image.

(Position Matching)

Figure 7:
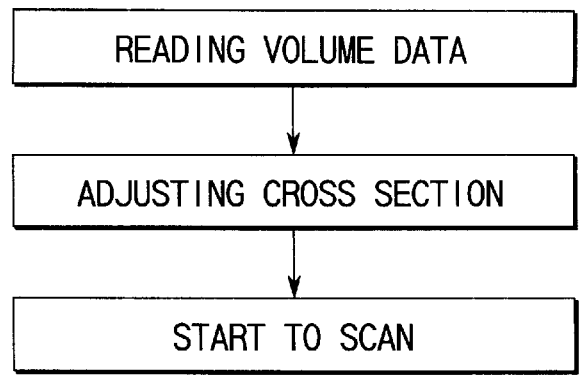
FIG. 7 is a flow chart showing a procedure of matching the coordinate system of volume data of a volume memory unit shown in FIG. 6 with the coordinate system of a position detection device 24.
Figure 8A:
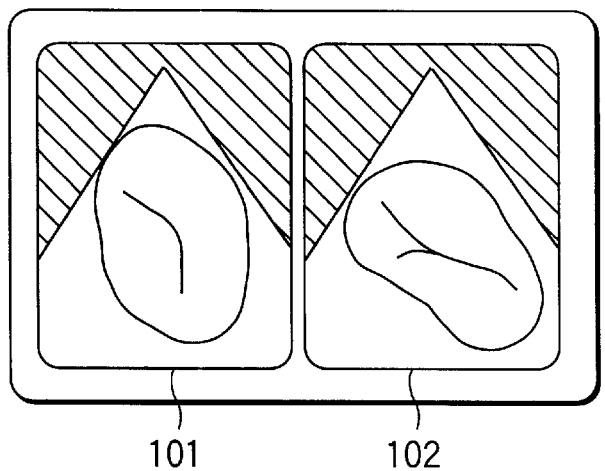
FIG. 8A is a view for supplementing the position matching process according to the second embodiment, which shows a parallel display example of a real-time image before matching and an image cut out from volume data.
Figure 8B:
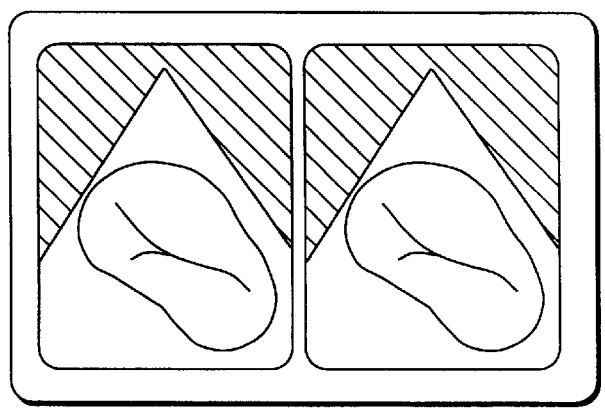
FIG. 8B is a view for supplementing the position matching process according to the second embodiment, which shows the parallel display example of the real-time image before matching and the image cut out from volume data.

As described above, tomographic image data in the same slice as a slice that is being scanned in real time is reconstructed from the stored volume data. For this purpose, the position of the reconstruction slice must be matched with the position of the real-time scanning plane. FIG. 7 shows this procedure. First, as shown in FIG. 8A, a real-time tomographic image 101 is displayed simultaneously with a tomographic image 102 reconstructed in an appropriate slice from the volume data. Next, while fixing the probe 1, the operator compares the two images and rotates the position of the slice to be reconstructed from the volume data about X-, Y-, and Z-axes, and/or moves the position parallel, by using a keyboard 23 or a trackball 22, such that the reconstructed tomographic image becomes an image concerning substantially the same slice as the real-time tomographic image. Consequently, the position matching (adjusting slice) is completed, and the tomographic image to be reconstructed on the basis of the volume data also changes in accordance with the movement of the scanning plane consistent with the motion of the probe 1.

(Applications of Second Embodiment)

The second embodiment can be used in various applications by changing the volume data to be stored in the volume memory unit 32 of an apparatus main body 20. For example, when past data of the same patient is held as the volume data, the transition of a lesion can be easily recognized by comparing tomographic images, before and after a treatment, in the same slice. Also, when data of a healthy person is held as the volume data, a lesion can be readily found by comparing a tomographic image in a certain slice of the patient with a tomographic image in the same slice of the healthy person.

(Modification of Second Embodiment)

Figure 9:
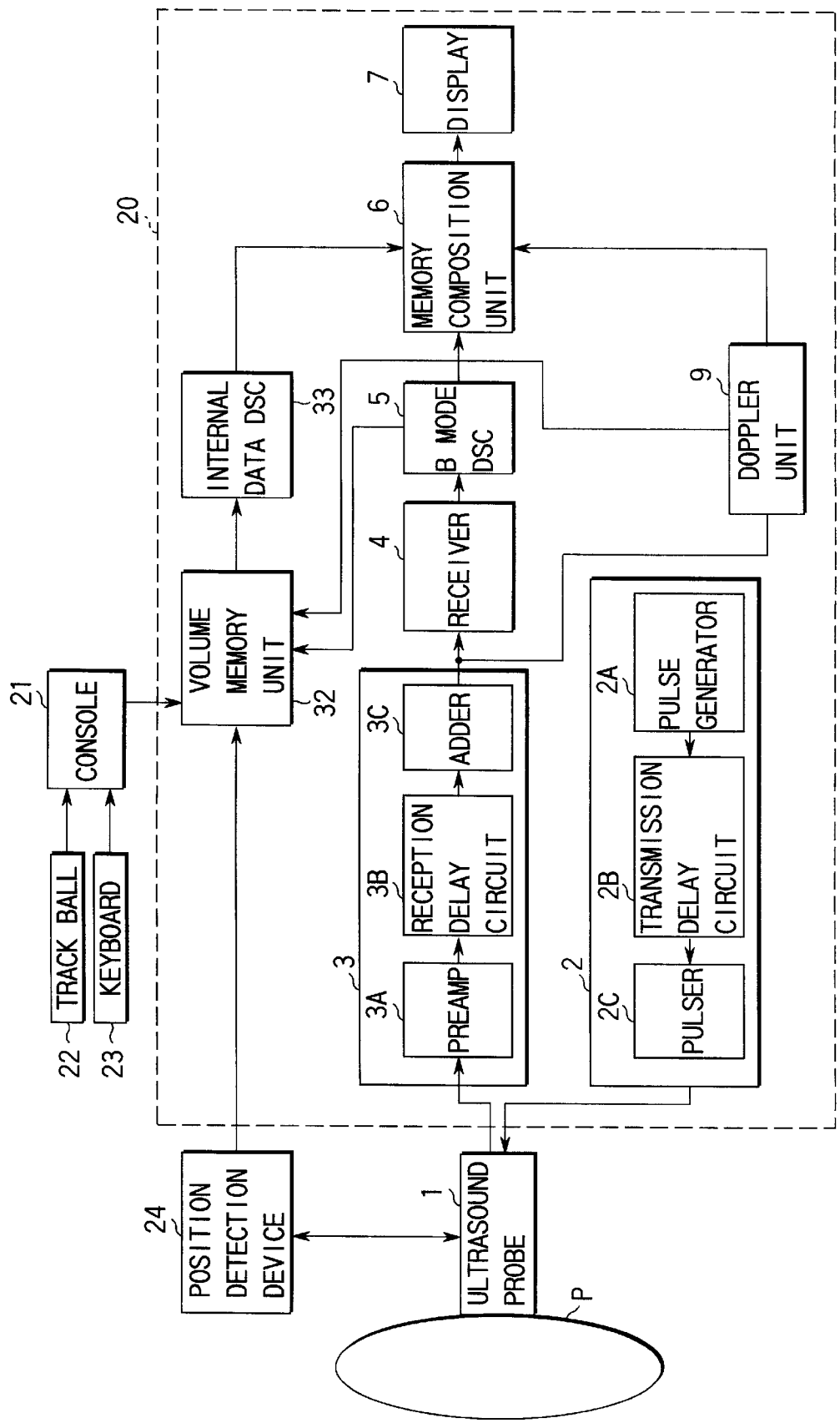
FIG. 9 is a block diagram showing the arrangement of an ultrasonic diagnostic apparatus according to a modification of the second embodiment of the present invention.
Figure 10A:
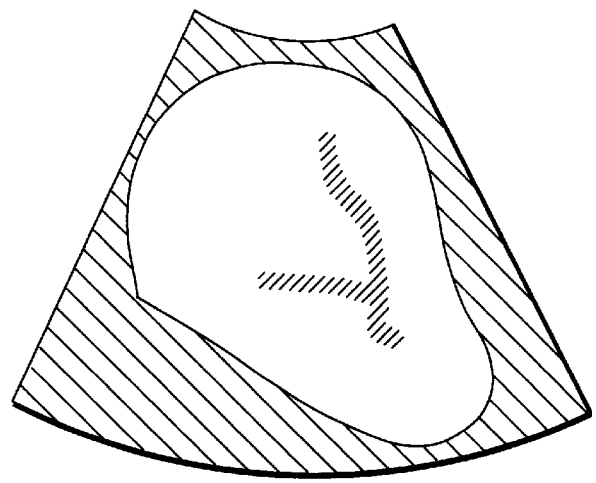
FIG. 10A is a view for supplementing a partial synthesizing process according to another modification of the second embodiment, which shows a display example of a real-time image before synthesis.
Figure 10B:
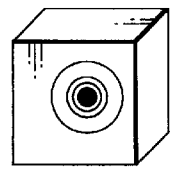
FIG. 10B is a view for supplementing the partial synthesizing process according to this modification of the second embodiment, which shows an example of a partial image of a portion of interest cut out from volume data.
Figure 10C:
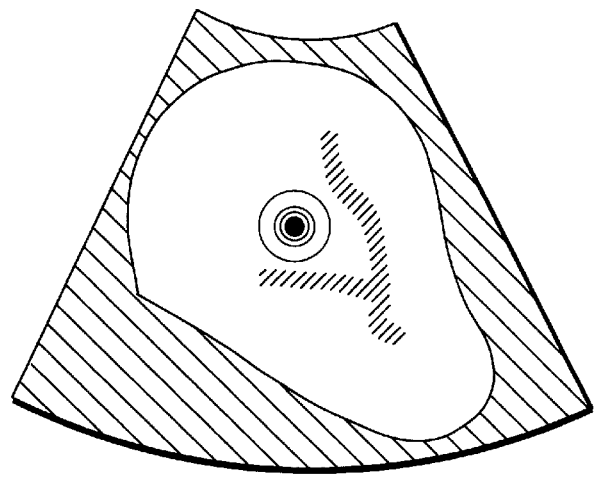
FIG. 10C is a view for supplementing the partial synthesizing process according to this modification of the second embodiment, which shows a synthetic display example of the partial image of the portion of interest cut out from volume data and fitted in the real-time image.

This embodiment can be modified as shown in FIG. 9. That is, the volume memory unit 32 stores data generated by scan immediately before examination of a patient currently being examined. This tomographic image data is supplied from a B mode digital scan converter 5 to the volume memory unit 32 and stored in it together with position information from the position detection device 24.

When data of the same patient collected immediately before diagnosis is held as the volume data, scanning of the same slice can be readily reproduced. That is, when a small lesion found during diagnosis is stored as an image, a correct scanning plane sometimes becomes uncertain even if an operator attempts scanning to check that again. Even in a case like this, a desired lesion can be found again by performing operation in relation to an image stored immediately before examination.

(Another Modification of Second Embodiment)

In this modification, the volume memory unit 32 stores data of occupying lesions such as primary hepatoma, metastatic cancer of the liver, gallstone, and hemangioma, or data of embryos. These data can be obtained by recording volume data of morbid organs from actual cases of lesions and partially extracting portions of interest. The data can also be imitative images of, e.g., lesions, formed using high-accuracy three-dimensional computer graphics or an image simulator.

On the basis of position information of a real-time scanning plane detected by the position detection device 24, partial tomographic image data of only a morbid organ pertaining to the same slice as the scanning plane is reconstructed from this volume data. The memory composition unit 6 fits this reconstructed partial tomographic image data into a corresponding portion of the tomographic image obtained in real time. This fitting process is done by replacing the real-time tomographic image data with the reconstructed partial tomographic image data. It is important to perform superposition or smoothing, rather than simple replacement, for number pixels on the boundary so that synthesis is performed as if the lesion is actually inserted into the organ of the object being examined in real time.

It is also important to eliminate a sense of incompatibility with the real-time tomographic image by controlling the image quality conditions of the reconstructed partial tomographic image data in accordance with console operations on the diagnostic apparatus. Usually, the gain, dynamic range, and the like of a diagnostic image are changed by an operator by using the console and set by the B mode digital scan converter 5. This information is simultaneously transmitted to the internal data digital scan converter 33 to allow the image qualities of the two images to change in association with each other.

Position matching between volume data and a real-time tomographic image is as described above. However, the main objective of this modification is to use the apparatus in training in which a trainee performs screening, as if a lesion actually exists, while observing a healthy object to be examined. Accordingly, position correction by the operator is to set only rough coordinates of the liver. After that, position information of volume data for a reconstructed image can also be randomly set within the range of the liver. Also, the volume memory unit 32 has a function of randomly selecting from a plurality of data different in size or disease name stored in it.

This allows training of finding and diagnosing a lesion to be performed by using a healthy person as an object to be examined. For example, when data of a different patient who has become ill is held as volume data, this modification can be used as educational simulation of ultrasonic examination by using a healthy person as an object.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnostic apparatus comprising:
   an ultrasonic probe;
   means for scanning a scanning plane inside an object to be examined with an ultrasonic beam via said ultrasonic probe and acquiring an echo signal;
   means for generating two-dimensional ultrasonic image data on the basis of the echo signal;
   display means for displaying the two-dimensional ultrasonic image data as a two-dimensional ultrasonic image;
   means for setting at least one point of interest or region of interest on the displayed two-dimensional ultrasonic image;
   means for detecting a three-dimensional position of the scanning plane;
   means for calculating a three-dimensional position of the point of interest or region of interest on the basis of the detected three-dimensional position of the scanning plane and the position of the point of interest or region of interest in the two-dimensional ultrasonic image;
   mark data generating means for, when the position of the scanning plane is changed, checking whether the set point of interest or region of interest is contained in the changed scanning plane, on the basis of the three-dimensional position of the changed scanning plane and the three-dimensional position of the set point of interest or region of interest, and generating first mark data representing the set point of interest or region of interest if the set point of interest or region of interest is contained in the changed scanning plane; and
   means for synthesizing the generated first mark data on tomographic image data corresponding to the changed scanning plane by performing position matching.

2. An apparatus according to claim 1, wherein the point of interest is set in an arbitrary point on the tomographic image in accordance with an instruction from an operator.

3. An apparatus according to claim 1, wherein the point of interest is continuously set on a boundary in an arbitrary region of the tomographic image in accordance with an instruction from an operator.

4. An apparatus according to claim 1, wherein the point of interest is set as a trace line representing a boundary of an arbitrary region of the tomographic image in accordance with an instruction from an operator.

5. An apparatus according to claim 1, wherein said mark data generating means checks whether the changed scanning plane is within a predetermined distance close to the set point of interest or region of interest, on the basis of the three-dimensional position of the changed scanning plane and the three-dimensional position of the point of interest or region of interest, and generates the first mark data if the changed scanning plane is within the predetermined distance close to the point of interest or region of interest.

6. An apparatus according to claim 1, wherein said mark data generating means checks whether the changed scanning plane is within a predetermined distance close to the set point of interest or region of interest, on the basis of the three-dimensional position of the changed scanning plane and the three-dimensional position of the point of interest or region of interest, and generates information representing that the changed scanning plane is within the predetermined distance close to the point of interest or region of interest if the changed scanning plane is within the predetermined distance close to the point of interest or region of interest.

7. An apparatus according to claim 1, wherein said mark data generating means checks whether the changed scanning plane is within a predetermined distance close to the set point of interest or region of interest, on the basis of the three-dimensional position of the changed scanning plane and the three-dimensional position of the point of interest or region of interest, and generates second mark data different in shape and/or color from the first mark data if the changed scanning plane is within the predetermined distance close to the point of interest or region of interest.

8. An apparatus according to claim 1, wherein the two-dimensional ultrasonic image is a B mode image representing a tissue structure by luminance.

9. An apparatus according to claim 1, wherein the two-dimensional ultrasonic image is a color Doppler image representing a blood flow distribution.

10. An ultrasonic diagnostic apparatus comprising:

an ultrasonic probe;

means for scanning a scanning plane inside an object to be examined with an ultrasonic beam via said ultrasonic probe and acquiring an echo signal;

means for generating two-dimensional ultrasonic image data on the basis of the echo signal;

means for detecting a three-dimensional position of the scanning plane;

means for storing volume data;

reconstructing means for reconstructing, from the volume data, two-dimensional image data pertaining to substantially the same plane as the scanning plane on the basis of the detected three-dimensional position of the scanning plane; and means for synthesizing the reconstructed two-dimensional image data on the two-dimensional ultrasonic image data by performing position matching.

11. An apparatus according to claim 10, wherein said reconstructing means changes the plane for reconstruction of the two-dimensional image data in accordance with a user instruction.

12. An apparatus according to claim 10, wherein the volume data is past data concerning the object.

13. An apparatus according to claim 10, further comprising means for generating the volume data from the two-dimensional ultrasonic image data.

14. An apparatus according to claim 10, further comprising means for inputting the volume data from an external device via a network.

15. An ultrasonic diagnostic apparatus comprising:

an ultrasonic probe;

means for scanning a scanning plane inside an object to be examined with an ultrasonic beam via said ultrasonic probe and acquiring an echo signal;

means for generating two-dimensional ultrasonic image data on the basis of the echo signal;

means for detecting a three-dimensional position of the scanning plane;

means for storing volume data;

reconstructing means for reconstructing, from the volume data, partial image data pertaining to substantially the same plane as the scanning plane on the basis of the detected three-dimensional position of the scanning plane; and means for synthesizing the reconstructed partial image data on the two-dimensional ultrasonic image data by performing position matching.

16. An apparatus according to claim 15, wherein the partial image data is image data pertaining to a lesion or an embryo.

17. An apparatus according to claim 15, wherein the partial image data is an imitative image of a lesion generated by three-dimensional computer graphics or an image simulator.

18. An apparatus according to claim 15, further comprising means for matching image qualities of the partial image data and the two-dimensional ultrasonic image data.

* * * * *